(12) United States Patent
Toyoda et al.

(10) Patent No.: US 6,445,565 B1
(45) Date of Patent: Sep. 3, 2002

(54) CAPACITIVE MOISTURE SENSOR AND FABRICATION METHOD FOR CAPACITIVE MOISTURE SENSOR

(75) Inventors: Inao Toyoda, Okazaki; Hajime Matsuhashi, Nagoya, both of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 10/043,106

(22) Filed: Jan. 14, 2002

(30) Foreign Application Priority Data

Feb. 15, 2001 (JP) ......................................... 2001-039001

(51) Int. Cl.⁷ ................................................. H01G 4/06
(52) U.S. Cl. ...................... 361/303; 361/311; 361/313; 257/301
(58) Field of Search ............................. 361/306.3, 313, 361/329, 303, 311; 257/301, 307, 308, 309

(56) References Cited

U.S. PATENT DOCUMENTS

| | | | |
|---|---|---|---|
| 4,057,823 A | * 11/1977 | Burkhardt et al. | .......... 257/414 |
| 4,144,636 A | 3/1979 | Burkhardt et al. | |
| 4,305,112 A | 12/1981 | Heywang et al. | |
| 4,893,214 A | 1/1990 | Nishiwaki et al. | |

FOREIGN PATENT DOCUMENTS

| | | |
|---|---|---|
| GB | 2149922 A | 6/1985 |
| JP | U-57-130257 | 8/1982 |
| JP | A-59-112256 | 6/1984 |
| JP | A-61-281958 | 12/1986 |
| JP | A-2-93357 | 4/1990 |
| JP | U-5-23124 | 3/1993 |
| JP | B2-6-105235 | 12/1994 |
| JP | A-7-20080 | 1/1995 |
| JP | B2-3042992 | 3/2000 |

* cited by examiner

*Primary Examiner*—Anthony Dinkins
(74) *Attorney, Agent, or Firm*—Law Offices of David G. Posz

(57) ABSTRACT

A capacitive moisture sensor is made from an SOI, i.e., silicon-on-insulator, substrate. Two electrodes, between which moisture-sensitive material is interposed, are formed from a thick silicon layer of the SOI substrate by separating the layer with a trench vertically reaching an insulator layer of the SOI substrate. Two substantially vertical sidewalls defining the trench make up a capacitor for moisture sensing. Therefore, by using deep trench, i.e., thick silicon layer, capacitance sensitivity to moisture is readily increased without horizontally widening the electrode or using horizontal surface of the electrode, that is, without enlarging sensor size or complicating fabrication process. In addition, the electrodes are made of silicon, so that corrosion resistivity against moisture is significantly.

20 Claims, 3 Drawing Sheets

CAPACITIVE MOISTURE SENSOR AND FABRICATION METHOD FOR CAPACITIVE MOISTURE SENSOR

CROSS REFERENCE TO RELATED APPLICATION

This application is based on and incorporates herein by reference Japanese Patent Application No. 2001-39001 filed on Feb. 15, 2001.

1. Field of the Invention

The present invention relates to a capacitive moisture sensor and a fabrication method for the sensor. The capacitive moisture sensor includes a pair of electrodes facing each other with moisture-sensitive material interposed therebetween, whose dielectric constant varies in response to ambient moisture. Ambient moisture is sensed on a basis of the capacitance between the electrodes, which is correlated with the dielectric constant.

2. Background of the Invention

A capacitive moisture sensor is utilized to measure indoor moisture for an air conditioner, outdoor moisture for meteorological observation, and so on. A capacitive moisture sensor that is highly sensitive, compact, reliable, and produced at low costs is demanded.

In order to increase the capacitance sensitivity between the electrodes, it is necessary to increase the size of the surfaces of the electrodes, which face each other. In proposed capacitive moisture sensors such as in JP-U-5-23124 and JP-A-64-86053, the two electrodes are formed from a metal film deposited on the surface of an insulator. Therefore, if it is possible to use only a vertical side wall of a thick metal film as the facing surfaces of the electrodes, the area size is significantly increased with simple configuration and compact size. However, in the proposed sensors, the two electrodes are formed from a thin metal film, so that the thickness of the thin film is restricted by film forming method, etching method, increased film internal stress, film brittleness due to the stress, or the like. Therefore, to provide sufficient facing area, it is necessary to extend horizontally the electrodes or use the horizontal surface of the electrodes. As a result, the sensor becomes bulky, or the fabrication process becomes complicated.

In addition, in the proposed capacitive moisture sensors, the electrodes are made of metal, so that the electrodes are vulnerable to corrosion caused by moisture.

SUMMARY OF THE INVENTION

The present invention has been made in view of the above aspects with an object to provide a capacitive moisture sensor that is preferably sensitive, compact, reliable, and produced at low costs.

In the present invention, a capacitive moisture sensor is made from an SOI, i.e., silicon-on-insulator, substrate, and electrodes for moisture sensing are formed from a thick silicon layer. For example, the thickness may be as thick as 10–15 $\mu$m and may be thicker. Thereby, the area of the electrodes facing each other is drastically enlarged in comparison with those of the proposed sensors. That is, the sensitivity to moisture in the capacitance between the electrodes is readily increased without horizontally widening the electrodes, namely, without enlarging sensor size. In addition, the electrodes are made of silicon, so that corrosion resistivity against moisture is significantly improved in comparison with the proposed metal electrodes.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENT

The present invention will be described in detail with reference to various embodiments.

(First Embodiment)

Figure 1:
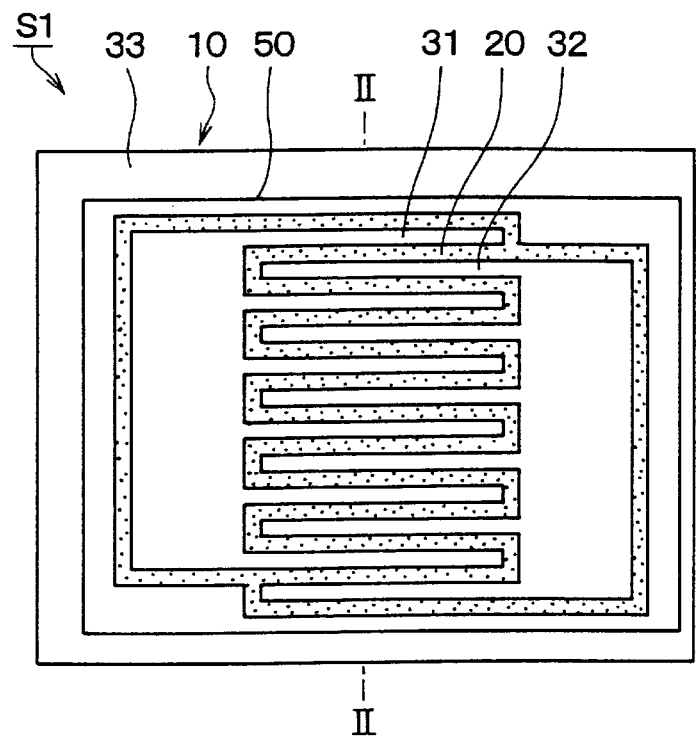
FIG. 1 is a plan view of a capacitive moisture sensor according to a first embodiment of the present invention.
Figure 2:
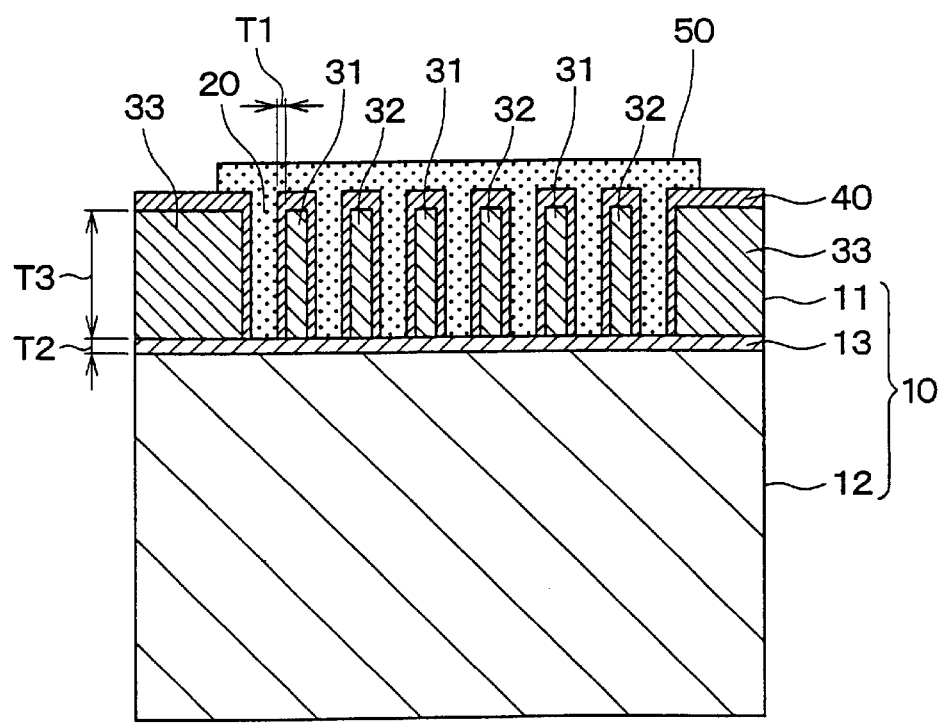
FIG. 2 is a cross-sectional view of the capacitive moisture sensor taken along the line II—II in FIG. 1.
Figure 3A:
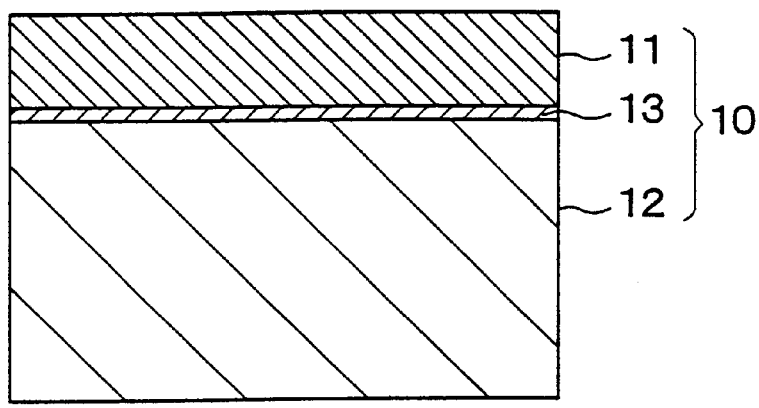
FIGS. 3A to 3C are cross-sectional views showing a fabrication method for the capacitive moisture sensor shown in FIG. 1.

The capacitive moisture sensor 1 shown in FIGS. 1 and 2 is formed from a built-up substrate 10 shown in FIG. 3A, which is constituted of a first semiconductor layer 11, a second semiconductor layer 12, and an insulator film 13 interposed therebetween. In the present embodiment, the first semiconductor layer 11 and the second semiconductor layer 12 are made of single crystal silicon, and the insulator film 13 is made of silicon oxide. Namely, an SOI, i.e., silicon-on-insulator substrate is applied to the built-up substrate 10.

As shown in FIG. 2, the sensor 1 has a trench 20 vertically reaching the insulator film 13 in the first semiconductor layer 11. The first semiconductor layer 11 is separated into at least two isolated regions that are insulated from each other by the trenches 20. In this embodiment, the isolated regions are a frame part 33 located in the periphery of the first semiconductor layer 11 and two electrode parts 31, 32 located inside the frame part 33. The trenches 20 are packed with moisture-sensitive material 50 whose dielectric constant varies in response to moisture. In this embodiment, as a preferable example, a surface insulator film 40 is formed on horizontal and vertical surfaces of the three isolated regions. The surface insulator film 40 may be made of silicon oxide, silicon nitride or the like. In this embodiment, the surface insulator film 40 is thermal silicon oxide film made by oxidizing the silicon making up the first semiconductor layer 11.

Moisture sensing is based on the capacitance between the two electrode parts 31, 32, which is correlated with ambient moisture. The two electrode parts 31, 32 are shaped in a comb and interleave each other. With a comb-shaped electrode configuration, the area occupied by the electrodes is minimized, and the facing area size of the electrode part 31, 32 is maximized.

Hygroscopic organic polymers such as polyimide and cellulose acetate butyrate may be used for the moisture-sensitive material 50. In this embodiment, polyimide is used. Because water molecules have high polarity, the dielectric constant of the material 50 changes significantly in response to water content in the material 50 and so does the capacitance of the sensor 1. Therefore, in this capacitive moisture sensor 1, it is possible to sense accurately ambient moisture by converting the capacitance between the two electrode parts 31, 32 to a corresponding electrical signal with a detection circuit. For example, a switched capacitor circuit is applicable to convert the capacitance to voltage. The detection circuit may be integrated in the built-up substrate 10 or may be formed separately.

It is preferable that the thickness T1 of the surface insulator film 40, which is formed on the surface of the electrode part 31, 32, is thinner than the thickness T2 of the insulator film 13. For example, if the thickness T3 of the first semiconductor layer 11 is 10–15 $\mu$m, the thickness T1 of the surface insulator film 40 may be thinner than 0.5 $\mu$m and the thickness T2 of the insulator film 13 may be 1.5–2 $\mu$m. Thereby, the parasitic capacitance between the electrode part 31, 32 and the second semiconductor layer 12 becomes lower than that between the two electrode parts 31, 32, so that the influence of the parasitic capacitance on sensor output is reduced.

Figure 3B:
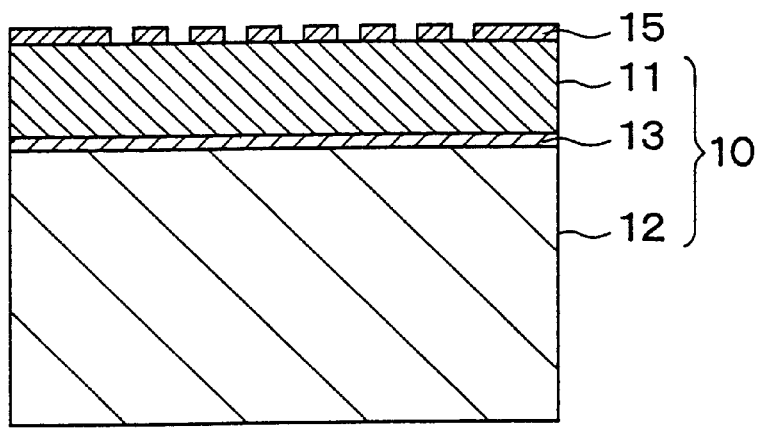
Figure 3C:
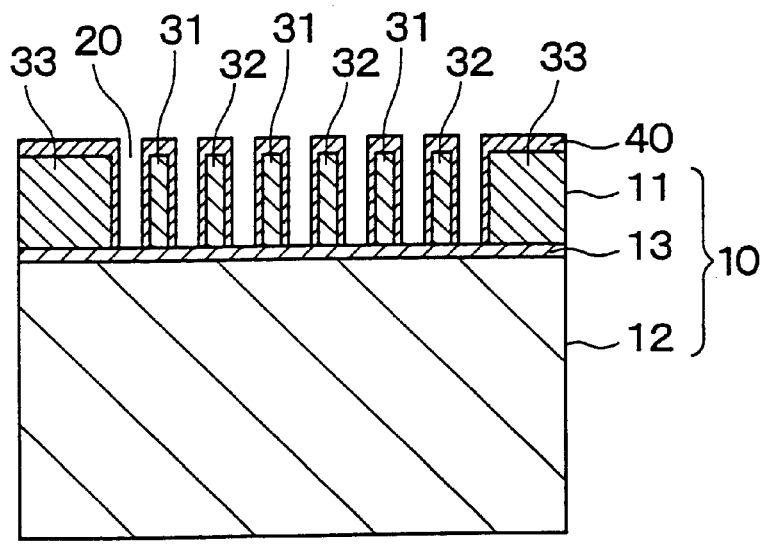

The fabrication process of the capacitive moisture sensor 1 will be explained in detail hereinafter with reference to FIGS. 3A to 3C. The built-up substrate 10 is prepared, as shown in FIG. 3A. As shown in FIG. 3B, the silicon oxide film 15 is formed on the surface of the first semiconductor layer 11 by means of thermal oxidization, sputtering, vacuum evaporation or the like. Afterward, a part of the silicon oxide film 15, where the trench 20 is formed later, is eliminated by photolithography and etching or the like. As shown in FIG. 3C, the trench 20 vertically reaching the insulator film 13 is formed in the first semiconductor layer 11 by anisotropic etching such as reactive-ion-etching. Thereafter, the surface insulator film 40 is formed on the sidewall defining the trench 20 by thermal oxidization. The silicon oxide film 15 becomes a part of the surface insulator film 40 after this oxidization. Subsequently, the moisture-sensitive material 50 is packed in the trench 20. The following procedures are applicable to pack the material 50 in the trench 20. Photosensitive polyimide is spin-coated and cured as a material for the moisture-sensitive material 50, thereafter the polyimide is defined by photolithography and etching. Alternatively, the moisture-sensitive material 50 is printed on predetermined area and cured. The moisture-sensitive material 50 is effectively packed in the trench 20 in collaboration with bubble removal under low pressure atmosphere after the moisture-sensitive material is spin-coated or printed over the trench. The bubble removal under low pressure atmosphere is effective to eliminate air bubbles trapped under the liquid material 50 in the trench 20 and thereby to fill out completely the trench with the material 50.

By the steps described above, the capacitive moisture sensor 1 shown in FIG. 2 is provided. Afterward, predetermined regions of the film 40 are opened to form a contact hole (not illustrated) by means of photolithography and etching. Through the contact hole, the electrode communicates with a metal pad (not illustrated) made of aluminum or the like for picking up sensor signals. The metal pad may be formed as follows as well. After the process shown in FIG. 3B, the metal pad is formed by means of metallization such as sputtering and vacuum evaporation in combination with photolithography and etching. Subsequently, as shown in FIG. 3C, the surface insulator film 40 made of silicon oxide, silicon nitride or the like is formed by sputtering after forming the trench 20. Afterward, predetermined regions of the film 40 are opened by means of photolithography and etching to let the pads communicate with the outside for picking up sensor signals.

In the capacitive moisture sensor 1, the film thickness T3 of the first semiconductor layer 11 may be as thick as 10–15 $\mu$m, and more thicker. Even if the layer 11 has that thickness, the trench 20 is readily formed by anisotropic etching. Namely, according to this embodiment, the facing area size of the electrode part 31, 32 is readily enlarged by thickening the first semiconductor layer 11 and deepening the trench 20 without horizontally widening the electrode part 31, 32.

Thereby, sensitivity of sensor 1 is significantly improved. In addition, in this embodiment, the electrode part 31, 32 is made of silicon, so that corrosion resistivity is significantly improved in comparison with metal electrodes in the proposed sensors.

Thus, according to the present embodiment, it is possible to provide the capacitive moisture sensor 1 that is compact and has preferable sensitivity to moisture and reliability. In addition, according to the fabrication method described above, it is possible to use ordinary semiconductor production processes such as thermal oxidation, sputtering, vacuum evaporation, photolithography, and anisotropic etching to fabricate the capacitive moisture sensor 1. Therefore, the present embodiment is suitable for mass production of moisture sensors with low costs.

In this embodiment, it is possible to omit the surface insulator film 40 on the sidewall of the trench 20, which is the facing area of the electrode part 31, 32, and to let the material 50 contact directly the electrode part 31, 32. However, corrosion resistivity against moisture is relatively diminished, although the electrode part 31, 32 made of silicon is much more corrosion-proof than the metal electrodes in the proposed sensors. There is a possibility of corrosion in such a harsh environment as alkaline atmosphere. Therefore, it is preferable to form the surface insulator film 40.

(Second Embodiment)

Figure 4:
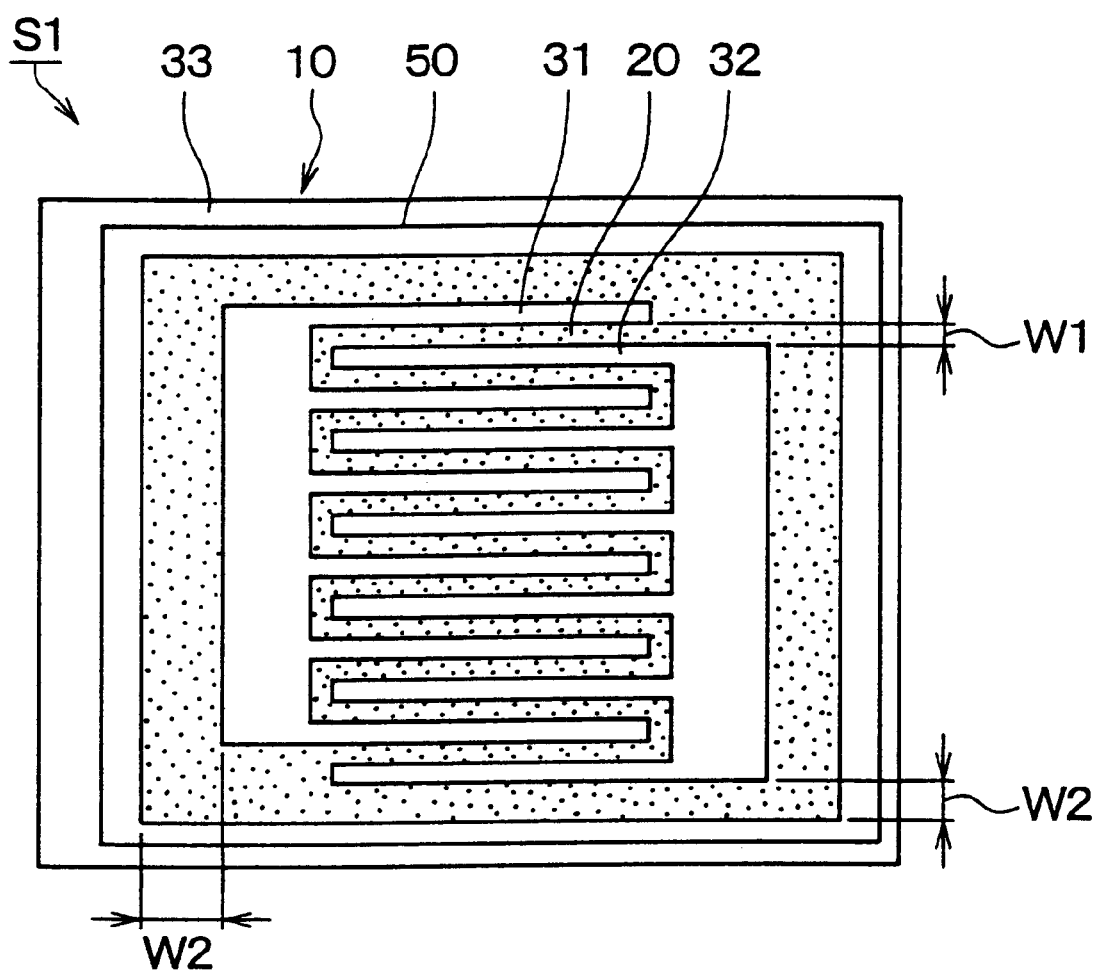
FIG. 4 is a plan view of a capacitive moisture sensor according to a second embodiment of the present invention.

In the first embodiment, the trench 20 of the capacitive moisture sensor 1 has a constant width irrespective of position, as shown in FIG. 1. In contrast, in a second embodiment, the trench 20 of the capacitive moisture sensor 2 has variations in the width thereof, as shown in FIG. 4. The width W1 of the trench 20 between the two electrode parts 31 and 32 is narrower than the width W2 of the trench 20 between the electrode part 31, 32 and the frame part 33. According to the second embodiment, the same function as in the first embodiment is provided with the following additional advantage. The parasitic capacitance between the electrode part 31, 32 and the frame part 33 is smaller than the capacitance between the two electrode parts 31 and 32, so that the influence of the parasitic capacitance on sensor output is reduced.

The above embodiments may be modified further within the spirit of the present invention. For example, the material 50 in the above embodiments does not have to cover the frame part 33 as long as at least the trench 20, whereby the capacitance between the two electrode parts 31, 32, is substantially determined, is packed with the moisture-sensitive material 50. In addition, it is possible to omit the frame part 33.

What is claimed is:

1. A capacitive moisture sensor comprising:
   a first semiconductor layer;
   a second semiconductor layer;
   an insulator film interposed between the first and the second semiconductor layers; and
   a moisture-sensitive material whose dielectric constant varies in response to moisture, wherein:
   a trench vertically reaching the insulator film is formed in the first semiconductor layer;
   the first semiconductor layer is separated into at least two isolated regions by the trench; and
   the moisture-sensitive material is packed in the trench.

2. The capacitive moisture sensor as in claim 1, wherein:
   the first and the second semiconductor layers are made of silicon.

3. The capacitive moisture sensor as in claim 1, wherein:
the moisture-sensitive material is a hygroscopic organic polymer.

4. The as capacitive moisture sensor in claim 1, wherein:
the isolated regions are a frame part located in a periphery of the first semiconductor layer, and a pair of electrode parts located inside the frame part to produce a sensor output signal based on capacitance between the two electrode parts; and
a width between the two electrode parts is narrower than a width between the electrode parts and the frame part.

5. The capacitive moisture sensor as in claim 1, further comprising:
another insulator film formed on a surface of each isolated region.

6. The capacitive moisture sensor as in claim 5, wherein:
the another insulator film is made of silicon oxide.

7. The capacitive moisture sensor as in claim 5, wherein:
the another insulator film is thinner than the insulator film interposed between the first and the second semiconductor layers.

8. A fabrication method for the capacitive moisture sensor as in claim 1, wherein:
the trench is formed by anisotropic etching.

9. The fabrication method as in claim 8, wherein:
the moisture-sensitive material is packed in the trench in collaboration with bubble removal under low pressure atmosphere after the moisture-sensitive material is coated over the trench.

10. The capacitive moisture sensor as in claim 1, wherein:
the first and second semiconductor layers are made of single crystal silicon.

11. The capacitive moisture sensor as in claim 1, wherein:
a side wall of each insulated region is substantially perpendicular to a horizontal surface of the isolated region.

12. The capacitive moisture sensor as in claim 4, wherein:
a vertical width of each electrode part is larger than a horizontally minimum width of the electrode part.

13. A fabrication method for a capacitive moisture sensor, the method comprising steps of:

forming a thick semiconductor layer having a predetermined thickness on an insulator layer:
forming a trench having a predetermined width, vertically reaching the insulator layer, and separating the semiconductor layer into at least two isolated regions including a pair of electrode parts to produce a sensor output signal based on capacitance between the electrode parts: and
packing the trench with a moisture-sensitive material whose dielectric constant varies in response to moisture.

14. The fabrication method as in claim 13, wherein:
the semiconductor layer is made of silicon; and
the moisture-sensitive material is a hygroscopic organic polymer.

15. The fabrication method as in claim 13, wherein:
the isolated regions further includes a frame part located in a periphery of the semiconductor layer, inside which the electrode parts are located; and
a width between the electrode parts is narrower than a width between the electrode part and the frame parts.

16. The fabrication method as in claim 13, further comprising a step of:
forming another insulator film of silicon oxide on a surface of each isolated region.

17. The fabrication method as in claim 13, wherein:
the trench is formed by anisotropic etching.

18. The fabrication method as in claim 13, wherein:
the moisture-sensitive material is packed in the trench in collaboration with bubble removal under low pressure atmosphere after the moisture-sensitive material is coated over the trench.

19. The fabrication method as in claim 13, wherein:
a side wall of each isolated region is substantially perpendicular to a horizontal surface of the isolated region.

20. The fabrication method as in claim 13, wherein:
a vertical width of each electrode part is larger than a horizontally minimum width of the electrode part.

* * * * *